(12) United States Patent
Copland, III et al.

(10) Patent No.: US 7,528,133 B1
(45) Date of Patent: May 5, 2009

(54) USE OF THIAZOLIDINEDIONES DERIVATIVES FOR PREVENTING UTERINE CONTRACTIONS IN PREMATURE LABOUR OR LACTATION

(75) Inventors: John A. Copland, III, Houston, TX (US); Kirk L. Ives, Dickinson, TX (US); Melvyn Soloff, Galveston, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 0 days.

(21) Appl. No.: 10/069,744

(22) PCT Filed: Oct. 29, 1999

(86) PCT No.: PCT/US99/25433

§ 371 (c)(1),
(2), (4) Date: Jul. 5, 2002

(87) PCT Pub. No.: WO00/25781

PCT Pub. Date: May 11, 2000

Related U.S. Application Data

(60) Provisional application No. 60/106,133, filed on Oct. 29, 1998.

(51) Int. Cl.
| | |
|---|---|
| *A61K 31/50* | (2006.01) |
| *A61K 31/501* | (2006.01) |
| *A61K 31/47* | (2006.01) |
| *A61K 31/445* | (2006.01) |
| *A61K 31/41* | (2006.01) |
| *C07D 239/42* | (2006.01) |
| *A01N 43/76* | (2006.01) |

(52) U.S. Cl. .................. 514/252.01; 514/342; 514/360; 514/369; 514/309; 514/375; 514/256

(58) Field of Classification Search ................. 514/252, 514/256, 342, 360, 309, 369, 375, 376, 252.01
See application file for complete search history.

(56) References Cited

U.S. PATENT DOCUMENTS 5,370,135 A * 12/1994 Dullien ....................... 128/898

(Continued)

FOREIGN PATENT DOCUMENTS

EP 0783888 7/1997

(Continued)

OTHER PUBLICATIONS

Hardman et al. "Goodman & Gilman's The Pharmacological Basis of Therapeutics" (9th ed, 1996) p. 51 and 57-58.*

(Continued)

*Primary Examiner*—San-ming Hui
(74) *Attorney, Agent, or Firm*—Fulbright & Jaworski, LLP

(57) ABSTRACT

The present invention provides methods of preventing or reducing oxytocin-mediated action by using a thiazolidinedione, such as troglitazone, or thiazolidinedione-like compounds. These methods describe the employment of these compounds alone or in combination with at least one other agent, such as a tocolytic agent. This offers a novel therapeutic regimen for the treatment of oxytocin-mediated actions, for example induction of uterine contractions, prostaglandin release, and milk letdown. Accordingly, conditions such as preterm labor and labor prior to Caesarian delivery can be treated by these methods.

14 Claims, 6 Drawing Sheets

U.S. PATENT DOCUMENTS 5,457,109 A * 10/1995 Antonucci et al. ....... 514/253.1

FOREIGN PATENT DOCUMENTS

| EP | 0861666 | 9/1998 |
|---|---|---|
| WO | WO 97/27191 | 7/1997 |
| WO | WO 98/39006 | 9/1998 |

OTHER PUBLICATIONS

Hanif el al. Molecular Pharmacology (1982), 22(2), 381-8.*
Cavaghan et al., Journal of Clinical Investigation, 1997;100(3):530-537.*
Towns et al., Endocrinology, 1994; 134(2):608-613.*
Copland et al., "Demonstation of functional oxytocin receptors in human breast Hs578T cells and their upregulation through a PKC-dependent pathway," *Endocrinology*, 140:2258-2267, 1999.
Dong et al., "Involvement of calcitonin gene-related peptide in the modulation of human myometrial contractility during pregnancy," *J. Clin. Invest.*, 104:559-565, 1999.
Fuchs et al., "Correlation between oxytocin receptor concentration and responsiveness to oxytocin in pregnant rat myometrium: effects of ovarian steroids," *Endocrinology*, 113:742-749, 1983.
Fuchs et al., "Oxytocin receptors and human parturition: a dual role for oxytocin in the initiation of labor," *Science*, 215:1396-1398, 1982.
Grazzini et al., "Inhibition of oxytocin receptor function by direct binding of progesterone," *Nature*, 392:509-512, 1998.
Hinko and Soloff, "Characterization of oxytocin receptors in rabbitt amnion involved in the production of $PGE_2$," *Endocrinology*, 130:3547-3553, 1992.
Hinko and Soloff, "Up-regulation of oxytocin receptors in rabbit amnion by glucocorticoids. Potentiation by cyclic adenosine 3',5' monophosphate," *Endocrinology*, 133:1511-1519, 1993.
Hoare et al., "The proximal portion of the cooH terminus of oxytocin receptor is required for coupling of Gg, but not Gi," *J. Biological Chem.*, 274:28682-28689, 1999.
Ip et al., "Antitumor efficacy in rats of CGP 19984, a thiazolidinedione derivative that inhibits luteinizing hormone secretion," *Cancer Res.*, 46:1735-1740, 1986.
Kimura et al., "Expression of oxytocin receptor in human pregnant myometrium," *Endocrinology*, 137:780-785, 1996.
Larcher et al., "Oxytocin receptor gene expression in the rat uterus during pregnancy and the estrous cycle and in response to gonadal steroid treatment," *Endocrinology*, 136:5350-5356, 1995.
Main, "Preterm Labor," The American College of Obstretricians and Gynecologists Technical Bulletin, No. 206, 1-10, Jun. 1995.
McCormick, "The contribution of low birth weight to infant mortality and childhood morbidity," *N. Engl. J. Med.*, 312:82-90, 1985.
Moise et al., "Indomethacin in the treatment of premature labor: effects on the fetal ductus arteriosus," *N. Engl. J. Med.*, 319:327-331, 1998.
Norton et al., "Neonatal complications after the administration of indomethacin for preterm labor," *N. Engl. J. Med.*, 329:1602-1607, 1993.
Postina et al., "Separate agonist and peptide antagonist binding sites of the oxytocin receptor defined by their transfer into the $V_2$ vasopressin receptor," *J. Biol. Chem.*, 271:31593-31601, 1996.
Reece and Homko, "Diabetes mellitus in pregnancy: what are the best treatment options?" *Drug Safety*, 18(3):209-220, 1998.
Soloff et al., "Endocrine control of parturition," *Biology of the Uterus* ($2^{nd}$ *Edition*), Wynn and Jollie (eds), Plenum Press, NY, pp. 559-607, 1989.
Soloff et al., "Oxytocin receptors: triggers for parturition and lactation?" *Science*, 204:1313-1315, 1979.
Strakova and Soloff, "Coupling of oxytocin receptor to G proteins in the rat myometrium during labor: $G_I$ receptor interaction," *Am. J. Physiol.*, 272:E870-E876, 1997.
Strakova et al., "ERK2 mediates oxytocin-stimulated PGE synthesis," *Am J. Physiol.*, 274:E634-E641, 1998.
Thornton et al., "Progesterone metabolite and spontaneous myometrial contractions in vitro," *The Lancet*, 353:1327-1329, 1999.
Wilkins et al., "Efficacy and side effects of magnesium sulfate and ritodrine as tocolytic agents," *Am. J. Ostet. Gynecol.*, 159:685-689, 1988.
Williams et al., "Nonpeptide oxytocin antagonists: analogs of L-371,257 with improved potency," *Bioorganic & Medicinal Chemistry Letters*, 9:1311-1316, 1999.

* cited by examiner

USE OF THIAZOLIDINEDIONES DERIVATIVES FOR PREVENTING UTERINE CONTRACTIONS IN PREMATURE LABOUR OR LACTATION

This application is a conversion of PCT/US99/25433 filed Oct. 29, 1999, which claims the benefit of U.S. provisional patent application Ser. No. 60/106,133 filed on Oct. 29, 1998, which is now abandoned. The entire text of the above-referenced disclosure is specifically incorporated by reference herein without disclaimer.

BACKGROUND OF THE INVENTION

I. Field of the Invention

The present invention relates generally to the field of medicine, including obstetrics. More particularly, it concerns the use of thiazolidinediones, including troglitazone, by itself and in combination with tocolytic agents to prevent or reduce oxytocin-mediated actions such as uterine contractions in premature labor and lactation.

II. Description of Related Art

Preterm birth causes at least 75% of neonatal deaths that cannot be attributed to congenital malformations. A newborn weighing less than 1500 grams is about 200 times more likely to die before becoming a year-old than an infant born with a birthweight of greater than 2500 grams. Preterm birth contributes significantly to developmental delay, visual and hearing impairment, chronic lung disease, and cerebral palsy. Low-birth-weight survivors also have a 10 times greater chance of being neurologically impaired. Even in healthy-appearing preterm infants, academic and family problems occur more frequently than they do with term infants (McCormick, 1985).

Even though preterm birth has continued to present significant problems in the field of obstetrics for many years, the rate of preterm births has remained at the same level since the middle of this century. Numerous and varied therapies are available but much controversy revolves around their efficacies in prevention of prematurity and the management of premature labor (Main, 1995). By controlling uterine contractions and allowing on time delivery, billions of dollars in care for premature infants will be saved.

Preterm labor, defined as spontaneous labor occurring prior to 37 weeks of gestation (with 39 weeks being term), accounts for approximately 1 in 10 births and is the cause of preterm delivery. Preterm delivery is associated with contractions of the uterine muscle, which are likely induced by oxytocin in the blood. Oxytocin action on the uterus is completely dependent upon the increased expression of oxytocin receptors (OTR) in the myometrium just prior to birth. The ability to inhibit the premature rise of OTR or inactivate OTR may be critical in preventing premature onset of labor and birth. The purpose of the invention is to prevent unwanted contractions by preventing an increase in OTR expression and/or preventing oxytocin from binding to OTR. Thus, the use of thiazolidinediones, such as troglitazone, or related compounds that prevent oxytocin from binding to OTR and/or inhibit an increase in OTR should prevent premature labor and labor prior to Caesarian delivery.

Known functions of oxytocin (OT) include smooth muscle contraction during birth (Fuchs et al., 1982; Soloff, 1989), milk ejection during lactation (Soloff, et al., 1979), and prostaglandin release (Hinko and Soloff, 1992). These actions occur as very specifically timed events because the upregulation of OTRs determines the responsiveness of cells to oxytocin. At term, myometrial OTRs rise 2-fold just before labor and fall dramatically immediately after birth. In contrast, OTRs in mammary myoepithelial cells, which contract in response to oxytocin that is reflexively released into the blood as a result of suckling, increase shortly after birth and remain elevated as long as suckling continues. From these two examples, it is clear that the rise in OTR levels dictate tissue specific OT action, and the regulation of OTRs in these two tissues is different. To date, known agents that cause an increase in OTR protein levels include estradiol in the uterus (Fuchs, et al., 1983; Larcher et al., 1995), and glucocorticoids and/or cyclic AMP in rabbit amnion (Hinko and Soloff, 1993), and glucocorticoids and an unknown protein(s) in a human breast tumor cell line, Hs578T (Copland et al., 1999).

OTRs are expressed on cell surface membranes, and the binding of OT from the circulation or arising from paracrine sources sets off a cascade of intracellular events that culminate in cell contraction and/or prostaglandin synthesis. These events are mediated by G proteins tethered to the intracellular portion of OTRs (Strakova and Soloff, 1997). $G_i$ and $G_q$ isotypes have been shown to be coupled to OTRs, and each works through distinct and separate intracellular pathways. Activation of these G proteins results in a rapid rise in intracellular calcium, phosphorylation of mitogen-activated protein (MAP) kinase (ERK 2 and p38) (Hoare et al., 1999). Other events resulting from OT treatment include transcriptional activation of cfos mRNA, a protein vital for cell cycle regulation (Strakova et al., 1998). No specific competitive antagonist exists for oxytocin because oxytocin and vasopressin share a high degree of homology with one another as well as the $V_{1a}$ vasopressin receptor and OTR (Postina et al., 1996 and references therein). Vasopressin at a 10-100 fold concentration will activate the oxytocin receptor. As well, a high affinity antagonist blocking oxytocin binding to the OTR exists but it binds equally well to the vasopressin receptor. Recently, Zingg described 5β-dihydroprogesterone, a progesterone metabolite, to noncompetively bind to the oxytocin receptor and antagonize oxytocin action (Grazzini et al., 1998). However, high concentrations of 100 μM 5β-dihydroprogesterone were needed to inhibit oxytocin induced uterine contractions (Thornton et al. 1999). A noncompetitive inhibitor (e.g. 5β-dihydroprogesterone) binds to a different site for instance on the OTR as opposed to the site that oxytocin binds to activate the OTR. A noncompetitive inhibitor alters the conformation of the molecule that it binds, thereby altering the ability of the activating ligand to bind to the same molecule. These events are only partially reversible once the noncompetitive antagonist binds. Thus, no effective specific competitive antagonist exists clinically for oxytocin and the oxytocin receptor.

By controlling uterine contractions and allowing on time delivery, billions of dollars in costs for premature infant care will be saved. For oxytocin to have biological activity, oxytocin receptors (OTR) must increase. This occurs shortly before birth as well as during breast-feeding to allow secretion of the mother's milk. Mothers who wish not to breast feed their infants could take troglitazone to inhibit oxytocin action.

Troglitazone is currently used clinically in Type 2 diabetic patients to increase insulin sensitivity and thus, increase glucose uptake into cells (thiazolidinediones do not cause hypoglycemia). This drug is taken orally with excellent absorption into the blood stream and few side effects. Troglitazone is marketed for Sankyo by Parke-Davis in the United States. No significant side effects of this drug have been demonstrated with the exception that a small percentage of patients developed idiopathic liver intolerance.

SUMMARY OF THE INVENTION

The present invention involves the interaction of thiazolidinediones, such as troglitazone, with the oxytocin receptor (OTR). Thiazolidinediones or thiazolidinedione-like compounds can be used alone, in combination with other thiazolidinediones and/or thiazolidinedione-like compounds, and/ or with other compounds such as at least one tocolytic agent. The methods of the invention can be used to prevent or reduce oxytocin-mediated actions. It is contemplated that the methods described herein can be used for treating mammals, such as humans, as well as other animals.

In one embodiment of the present invention, methods are provided for preventing preterm labor in a pregnant subject by administering to the subject an amount of thiazolidinedione effective to prevent the subject from undergoing preterm labor.

In another embodiment, methods for reducing or preventing an oxytocin-mediated action in a subject comprising administering to the subject an amount of thiazolidinedione effective to reduce the oxytocin-mediated action in the subject. The present invention can be implemented to treat any oxytocin-mediated action, including induction of labor in a pregnant subject, induction of uterine cramps, induction of milk letdown, and induction of prostaglandin release.

In other embodiments of the present invention, the thiazolidinedione compound of the treatments described above comprises troglitazone. While in further embodiments, the thiazolidinedione comprises pioglitazone, BRL49653, or a compound related to troglitazone. A compound related to troglitazone is one that is substantially similar to the chemical structure of troglitazone or can be derived from troglitazone.

The methods of the present invention have clear therapeutic and preventative applications. As such, some embodiments of the present invention include a thiazolidinedione that is dispersed in a pharmacologically acceptable form so that the thiazolidinedione can be administered to a subject. Administration of the compound could be accomplished locally, parenterally, intravenously, or intravaginally. It is contemplated that intravaginal administration through the use of, for example, a suppository or cream formulation, provides therapeutic benefits for the treatment of uterine contractions.

While the methods of the present invention employs thiazolidinedione alone, it is further contemplated that the methods can be implemented using thiazolidinedione in combination with at least one other thiazolidinedione, a thiazolidinedione-like compound, or a tocolytic agent. Tocolytic agents have been used to relax the uterus, and in some embodiments of the present invention, the tocolytic agent comprises at least one beta-mimetic, magnesium sulfate, at least one prostaglandin inhibitor, or at least one calcium-blocking agent. In still further embodiments of the described invention, the prostaglandin inhibitor is indomethacin, whereas the calcium-blocking agent is nifedipine.

In the combination treatments of the present invention using both a thiazolidinedione and a tocolytic agent, in one embodiment of the invention, the compounds are administered to a subject at the same time, but in other embodiments, the thiazolidinedione is administered before the other tocolytic agent, and vice versa.

The present invention is also directed at methods of screening for antagonists and agonists of oxytocin since troglitazone was shown herein to bind the oxytocin receptor. In some embodiments, screening for an oxytocin agonist is done by administering a troglitazone-like compound to an oxytocin receptor and determining whether the compound binds the receptor. Measurable binding identifies the troglitazone-like compound as an agonist. In other embodiments, screening for an oxytocin antagonist is accomplished by at least (a) administering a thiazolidinedione to an oxytocin receptor; (b) administering a composition comprising a candidate oxytocin antagonist; and (c) determining whether the thiazolidinedione binds to the receptor.

The use of the word "a" or "an" when used in conjunction with the term "comprising" in the claims and/or the specification may mean "one," but it is also consistent with the meaning of "one or more," "at least one," and "one or more than one."

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

In FIG. 3A, cells were treated with 10 nM oxytocin demonstrating an increase in cytoplasmic calcium levels. In FIG. 3B, cells were pretreated with 0.001 microgram/ml troglitazone (2.2 nM) 1 minute prior to 10 nM oxytocin treatment. There is no effect of troglitazone at this concentration upon oxytocin-stimulated calcium transients. In FIG. 3C, a 0.01 microgram/ml (22.6 nM) troglitazone partially blocks oxytocin-induced calcium transients. In FIG. 3D, 0.1 microgram/ml (226 nM) troglitazone completely blocks 10 nM oxytocin-induced calcium transients but does not block 100 nM bombesin-induced calcium transients. This demonstrates specificity of troglitazone for oxytocin mediated action (also shown in FIG. 3G). In FIG. 3E, 100 nM oxytocin and 100 nM bradykinin induce a calcium transient in human myometrial cells. In FIG. 3F a 226 nM troglitazone does not block calcium transients induced by oxytocin and bradykinin whereas in FIG. 3G, 1 microgram/ml (2.2 micromolar) troglitazone specifically blocks oxytocin- but not bradykinin-induced calcium transients. In FIG. 3H, 100 nM and 1 micromolar troglitazone demonstrate a dose-dependent inhibition of the rise in oxytocin-induced calcium levels.

DESCRIPTION OF ILLUSTRATIVE EMBODIMENTS

Figure 1:
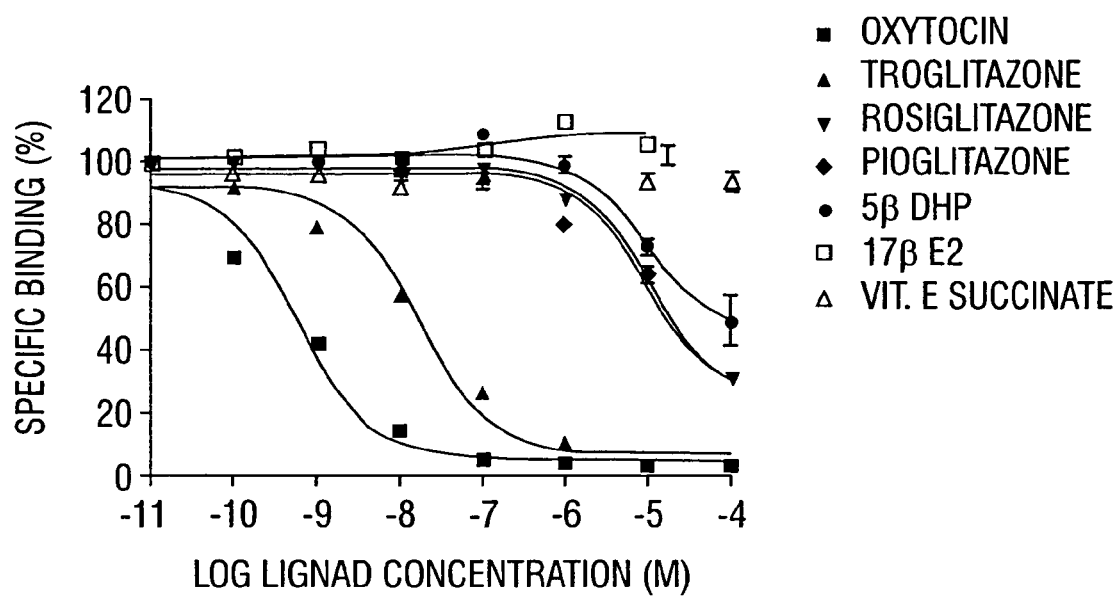
FIG. 1. Binding of thiazolidinediones to oxytocin receptors. Percent inhibition of $^{125}$I-OTA binding in human myometrial cells.

The present invention is based on the observation that thiazolidinediones, such as troglitazone, can inhibit the binding of oxytocin to the oxytocin receptor (OTR). Oxytocin binding triggers various oxytocin-mediated activities such as the onset of uterine contractions, and concomitantly the onset of labor, prostaglandin release, and milk letdown. Oxytocin causes prostaglandin release from the ovary and uterus. Prostaglandin $E_2$ and $F_\alpha$ may play a role in luteolysis and luteal phase defect. Thiazolidinediones, such as troglitazone, and thiazolidinedione-like compounds thus provide a therapeutic and prophylactic approach to inhibit any unwanted action of oxytocin or similar compounds that activates OTR, e.g., vasopressin. Exemplary thiazolidinediones are seen in U.S. Pat. No. 5,478,852 and U.S. Pat. No. 5,814,647, which are incorporated by reference herein.

The value of these treatments is large since approximately 10% of pregnant women deliver preterm (Norton et al., 1993; Main, 1995). To date, no studies convincingly demonstrate improved survival or any index of longterm neonatal outcome with the use of existing tocolytic (uterine relaxing) therapy. Many potential damages of tocolytic therapy to mother and neonate are well documented (Norton et al., 1993; Moise et al., 1998; Wilkins et al., 1988). Potential complications of beta-adrenergic agents include hyperglycemia, hypokalemia, hypotension, pulmonary edema, cardiac insufficiency, dysrhythmias, myocardial ischemia, and maternal death. Potential complications of magnesium sulfate include pulmonary edema, respiratory depression, cardiac arrest, maternal tetany, profound muscular paralysis, and profound hypotension. All but pulmonary edema are rare complications of this treatment. Potential complications of nifedipine treatment include transient hypotension. Thus, it is clear that additional methods for the treatment of preterm deliveries are needed.

I. OXYTOCIN-MEDIATED ACTIONS

It is the inventors' discovery that thiazolidinediones, such as troglitazone, can bind to the oxytocin receptor (OTR), and consequently, the present invention comprises inhibiting or reducing oxytocin-mediated actions.

Oxytocin is a short-lived, fast acting hormone, made by the hypothalamus of the brain, along with its close relative vasopressin (anti-diuretic hormone), stored in the posterior pituitary, and released into the blood as needed. It stimulates certain smooth muscle coats, constricts certain blood vessels and facilitates the sensitivity of some tissues to other hormones and nerves. The main tissues affected are the uterus, including endometrium and myometrium, vagina, breasts (both sexes), erectile tissue (both sexes), seminal vesicles, and with special-case effects on uterine muscle contractions in both birth and orgasm, the vascular constriction that lessens placental separation bleeding, and the let-down reflex that nursing mothers have when babies cry.

Oxytocin is produced in two discrete groups of neurons in the brain of all mammals. One group of oxytocin-producing neurons projects to the posterior pituitary, which is an endocrine gland located at the base of the brain. From the pituitary, oxytocin is released into the bloodstream, whereby it exerts the well-known peripheral effects like uterine contraction and milk let-down. The other group of oxytocin-containing neurons projects directly to specific brain areas that are known to mediate maternal behaviors. By acting locally as a chemical messenger in these brain areas, oxytocin acts as a regulator or controller of maternal behaviors.

Agents known to stimulate the release of oxytocin from the posterior pituitary include sensory stimuli arising from the cervix, vagina, and breast. Secretion of oxytocin is also stimulated by increases in the osmality of plasma. Secretion of oxytocin is suppressed by ethanol and ovarian relaxin. The present invention contemplates the use of agents that stimulate the release of endogenous oxytocin, as described above, as well as antagonists of agents that normally suppress the release of endogenous oxytocin.

Oxytocin is currently indicated for stimulation of uterine contraction to induce labor and for the control of postpartum hemorrhage following delivery of the placenta. It is also indicated for stimulation of lactation for breast-feeding. Oxytocin is currently prepared synthetically and sold under various trade names including Pitocin (Parke-Davis, Morris Plains, N.J.) and Syntocinon. It can be administered intravenously, intramuscularly, and by nasal absorption. Activity of oxytocin is expressed in terms of USP units, as defined in a bioassay of uterine-stimulating potency of posterior pituitary extracts. One USP unit is the equivalent of approximately 2 µg of pure peptide.

Oxytocin receptors (OTRs) are expressed on the cell surface membrane. The first three extracellular domains of OTR are crucial for high-affinity oxytocin binding and for selection of agonists (Postina et al., 1996). Oxytocin from the circulation or arising from paracrine derived sources interact with cell surface OTRs to set off a cascade of intracellular events. These events are mediated by G proteins tethered to the intracellular portion of OTRs (Strakova and Soloff, 1997). Subsequent activation of these G proteins result in a rapid rise in intracellular calcium and phosphorylation of MAP kinases (ERK 2). Other events resulting from oxytocin treatment include transcriptional activation of cfos mRNA, a protein vital for cell cycle progression (Strakova et al., 1998).

Oxytocin and oxytocin related compounds, acting through oxytocin receptors, are currently in clinical use for induction of uterine contractions and facilitation of delivery of a baby and placenta at the time of birth. This action is dependent upon the timely increase of OTRs (oxytocin receptors) on the target cell surface. Without an upregulation of OTRs, oxytocin has no action on the parturient uterus, thus limiting adverse side effects. During the latter stages of pregnancy, the number of OTRs increases, which ultimately causes the smooth muscle of the uterus to contract and lead to labor. The interaction between oxytocin and the OTR is also involved with uterine cramping generally, the promotion of milk glands to release milk (milk letdown), and prostaglandin release.

Examples of oxytocin agonists that would be preferred in the present invention include 4-threonine-1-hydroxy-deaminooxytocin, 9-Deamidooxytocin, an analog of oxytocin containing a glycine residue in place of the glycinamide residue (Ferrier and Du Vigneaud, 1966); 7-D-proline-oxytocin and its deamino analog (Ferraro and Du Vigneaud, 1966); (2,4-

Diisoleucine)-oxytocin, an analog of oxytocin with natriuretic and diuretic activities (Hruby et al., 1970); deamino oxytocin analog (Urry et al., 1970); a long-acting oxytocin (OT) analog 1-desamino-1-monocarba-E12-Tyr(OMe)]-OT (dCOMOT) (Veznik et al., 1979; Cort et al., 1982 and 1979); carbetocin, a long-acting oxytocin analog (Hunter et al., 1992); oxytocin agonist [Thr4-Gly7]-oxytocin (TG-OT) (Chadio and Antoni, 1993); oxytocin agonist as described by Olson et al., (1991); oxypressin, an equipotent analog of oxytocin and vasopressin (Gazis et al., 1987); and Deamino-6-carba-oxytoxin (dC60), a potent oxytocin analog considered to be resistant to some of the physiologically significant enzymic systems (Krejci et al., 1981). As well, nonpeptide oxytocin antagonists have been recently been described which include L-371,257, related series of compounds containing an ortho-trigluoroethoxyphenylacetyl core (e.g. L374,943) (Williams et al., 1999).

U.S. Pat. No. 5,846,766 relates to a receptor for a posterior pituitary hormone, oxytocin; a DNA sequence encoding for the receptor; a recombinant DNA molecule containing the DNA sequence and a transformant comprising the recombinant DNA molecule. The present invention further relates to methods of detection and diagnosis and a kit to aid in same which comprise either oxytocin, its receptor or antibodies to the receptor.

A. Preterm Labor/Caesarian Delivery

The present invention includes methods of preventing or reducing the risk of preterm delivery through the administration of thiazolidinediones such as troglitazone to a pregnant subject. Major changes in the function and structure of the uterus occur with respect to pregnancy. Until labor occurs, the uterus is mainly quiescent. At that point, heightened contractile activity involves raised levels of (i) oxytocin receptors; (ii) calcium channels; (iii) gap junctions; and (iv) endothelin receptors.

Preterm labor is generally characterized by regular uterine contractions accompanied by progressive cervical dilation and/or effacement prior to week 37 of gestation in humans. In most cases, the cause of preterm labor is not known, though some predisposing factors have been identified. Various circumstances such as multiple gestations and a history of second-trimester simultaneous abortion have been associated with its occurrence, in addition to some maternal activities.

Some methods exist for determining whether a patient is at risk for preterm delivery. One method involves testing for the presence of fetal fibronectin in the pregnant mother's cervical or vaginal secretions, which is an indicator of the possibility of preterm delivery (Lockwood et al., 1991). Alternatively, levels of salivary estriol has been used to distinguish true and false labor (U.S. Pat. No. 5,480,776) and to determine the effectiveness of tocolytic therapies for the postponement of labor (U.S. Pat. No. 5,370,135).

Some preventative therapies have been studied, although the efficacy of none of the approaches has been unequivocally established. For example, oral tocolytic therapy has been prescribed to prolong gestation, as has reduced activity for the mother. Thus, the present invention provides a much needed alternative to existing treatments in the prevention of preterm labor. Management of preterm labor has also been a subject of study where tocolysis treatments have been utilized with various degrees of effectiveness. No study has proven the long-term neonatal benefits of this therapy. Likewise, the present invention has utility with respect to management of preterm labor, by a regimen comprising at least one thiazolidinedione alone or in combination with other tocolytic agents.

As the present invention can inhibit or reduce uterine contractions through the administration of thiazolidinedione, such as troglitazone, or thiazolidinedione-like compounds, the methods of the present invention can be used to inhibit uterine contractions prior to Caesarian delivery (C-section), which refers to a surgical procedure in which an incision is made through the abdominal and uterine walls for delivery of a fetus. Furthermore, the methods of the invention can be used to treat dysmenorrhea, which describes painful menstruation.

B. Other Oxytocin-Mediated Actions

Another observation of the present invention relates to the ability of thiazolidinediones to prevent the release of prostaglandins by oxytocin. Prostaglandins comprise modified fatty acids that have a number of activities. Prostaglandins are cyclic, unsaturated fatty acids that are usually derived from arachidonic acid, a 20-carbon, straight-chain, polyunsaturated fatty acid precursor. Prostaglandins can act as potent vasodilators to relax muscles in the walls of blood vessels. In women, prostaglandins are involved in the control of gonadotropin releasing hormone (GnRH) over luteinizing hormone (LH) secretion, control of ovulation, and inducement of uterine contractility. Recent studies have indicated that inhibiting prostaglandin release can be an effective treatment for dysmenorrhea, while administration of prostaglandin results in inducement of labor or therapeutic abortions. Prostaglandins have also been implicated in the progression of cancer. As well, many tissues in which prostaglandins play a role in cancer progression such as colon and breast may also express oxytocin receptors. Recently, oxytocin receptors have been described in human breast tumors. Thus, an oxytocin antagonist may slow tumor progression by inhibiting prostaglandin synthesis.

To date, oxytocin is known to signal through calcium and MAP kinase pathways. New, not yet to be described pathways may be discovered that play critical roles in cell differentiation, cell proliferation, and apoptosis. A pure oxytocin antagonist could elucidate the role of oxytocin in these pathways.

C. Tocolytic Agents

In some embodiments of the present invention, a therapy to inhibit or reduce oxytocin-mediated action comprises administering a thiazolidinedione such as troglitazone and another tocolytic agent. A number of tocolytic (uterine relaxing) agents are in use to prevent uterine contractions. These include beta-mimetics, such as β-adrenoreceptor stimulants (for example, salbutamol, terbutaline, isoxsuprine, ritodrine, and fenoterol), magnesium sulfate, prostaglandin inhibitors (such as, indomethacin, aspirin, and naproxen), and calcium-blocking agents like nifedipine and nicardipine. Additionally, a candidate for tocolysis is the calcitonin gene-related peptide (CGRP), which is a powerful vasodilator that generally relaxes smooth muscle tissue and has been recently reported as inducing dose-dependent relaxation of spontaneously contracting myometrium in pregnant women (Dong et al., 1999; Yallampi et al., 1999, both incorporated herein by reference). It is contemplated that the thiazolidinedione and the other tocolytic agent may be administered simultaneously or at different times to inhibit or reduce uterine contractions or any other oxytocin-mediated action.

Tocolysis treatment usually employs the least amount of the tocolytic agent to effect reduction in the frequency of uterine contractions and stop cervical alterations. Tocolytic agents such as ritodrine and magnesium sulfate are generally given intravenously. Terbutaline, a beta-mimetic, is administered intravenously or subcutaneously. If intravenous treatment is successful, this is typically followed up with oral administration of ritodrine or terbutaline. Oral therapy can be used to maintain the effect until 35 to 37 weeks of gestation.

General contraindications to tocolysis for preterm labor include the following: acute fetal distress, chorioamnionitis, eclampsia or severe preeclampsia, fetal demise, fetal maturity, and maternal hemodynamic instability. Moreover, the following complications have been observed: for beta-adrenergic agents (beta-mimetics), hyperglycemia, hypokalemia, hypotension, pulmonary edema, cardiac insufficiency, arrhythmias, myocardial ischemia, and maternal death; for magnesium sulfate, pulmonary edema, respiratory depression, cardiac arrest, maternal tetany, profound muscular paralysis, and profound hypotension; for indomethacin, hepatitis, renal failure, and gastrointestinal bleeding; and for nifedipine, transient hypotension.

II. TROGLITAZONE AND OTHER THIAZOLIDINEDIONES

The methods of the present invention are directed at methods of inhibiting or reducing oxytocin-mediated action and generally treating a subject through the use of troglitazone, other thiazolidinediones, or thiazolidinedione-like compounds, some of which are described in U.S. Pat. No. 5,968,960, which is hereby incorporated by reference. Methods of making thiazolidinediones and thiazolidinedione-like compounds are described, for example, in U.S. Pat. No. 5,223,522 issued Jun. 29, 1993; U.S. Pat. No. 5,132,317 issued Jul. 12, 1992; U.S. Pat. No. 5,120,754 issued Jun. 9, 1992; U.S. Pat. No. 5,061,717 issued Oct. 29, 1991; U.S. Pat. No. 4,897,405 issued Jan. 30, 1990; U.S. Pat. No. 4,873,255 issued Oct. 10, 1989; U.S. Pat. No. 4,687,777 issued Aug. 18, 1987; U.S. Pat. No. 4,572,912 issued Feb. 25, 1986; U.S. Pat. No. 4,287,200 issued Sep. 1, 1981; U.S. Pat. No. 5,002,953, issued Mar. 26, 1991; U.S. Pat. Nos. 5,972,944; 5,965,589; 5,910,592; 5,811,439; 5,506,245; 4,340,605; 4,438,141; 4,444,779; 4,461,902; 4,703,052; 4,725,610; 4,897,393; 4,918,091; 4,948,900; 5,194,443; 5,232,925; and 5,260,445; WO 91/07107; WO 92/02520; WO 94/01433; WO 89/08651; and JP Kokai 69383/92, which are herein incorporated by reference.

Thiazolidinedione-like compounds include compounds with structural similarity to thiazolidinedione. Such a thiazolidinedione-like compound may comprise, or be composed entirely of, at least one derivative or mimic of at least one moiety that may be present in a thiazolidinedione. As used herein a "derivative" or "thiazolidinedione-like compound" refers to a chemically modified or altered form of a thiazolidinedione molecule, while the terms "mimic" or "analog" refers to a molecule that may or may not structurally resemble a thiazolidinedione molecule, but functions similarly to it. As used herein, a "moiety" generally refers to a smaller chemical or molecular component of a larger chemical or molecular structure, and is encompassed by the term "molecule."

Troglitazone (±5-[[4-[(3,4-dihydro-6-hydroxy-2,5,7,8-tetramethyl-2H-1-benzopyran-2-yl)methoxy]phenyl]methyl]-2,4-thiazolidinedione) has been used in the management of Type II diabetes as an antihyperglycemic agent. Insulin sensitivity is enhanced by it in muscle and adipose tissue, and troglitazone impedes hepatic gluconeogenesis. It has been used alone or in combination with a sulfonylurea to control adult-onset diabetes. It has a molecular weight of approximately 441 daltons and its formula is $C_{24}H_{27}NO_8S$. Polymorphic forms of troglitazone have also been described, such as in U.S. Pat. No. 5,700,820, which is herein incorporated by reference. BRL49563 (rosiglitazone BRL49653 or avandia, Smith-Kline recently introduced on market) and pioglitazone are second generation thiazolidinediones used in the treatment of type 2 diabetes. They were designed based on the structure of troglitazone and differ in that these two compounds do not contain the vitamin E moiety that is contained in troglitazone. BRL49653 and have a 100- and 6-fold higher affinity for the transcriptional factor PPARγ compared to that of troglitazone. Thus, in type 2 diabetes, 2-4 mg/day of BRL49563 (avandia, rosiglitazone) are used in patients as compared to 200-400 mg/day of troglitazone to lower blood glucose levels. It is important to note that thiazolidinediones do not cause hypoglycemia. These agents act to sensitize insulin's ability to cause blood glucose to be taken up into target cells e.g. adipocytes and muscle.

III. METHODS FOR ASSAYING TROGLITAZONE OR OTHER THIAZOLIDINEDIONE ACTIVITY

Because this invention is based on the observation that thiazolidinediones such as troglitazone both inhibit oxytocin from binding its receptor and bind to the receptor, binding assays present an embodiment for assaying thiazolidinedione activity. These binding assays are well known to those of skill in the art, as represented by Hoare et al., 1999 and Postino et al., 1996, which are herein incorporated by reference. Such assays can be used to evaluate the efficacy of thiazolidinedione therapy; alternatively, these assays can be used with the screening methods of the present invention to identify and characterize agonists and antagonists of oxytocin. An "agonist" is used herein to refer to a compound or substance that can bind to a receptor and activate a signalling pathway. With respect to the present invention, an agonist would be capable of binding the oxytocin receptor and mimic the function of oxytocin. Because thiazolidinediones bind OTRs, it is contemplated that the structure of thiazolidinediones can serve the basis for this interaction. Other thiazolidinedione-like substances may serve as agonists, and any oxytocin agonist activities can be evaluated in an OTR binding assay.

An "antagonist" of the present invention is a substance or compound that competes with another substance, such as a thiazolidinedione, for binding to a receptor, for example the OTR. Antagonists can be screened according to the present invention by assaying for competition between the candidate antagonist and a thiazolidinedione for binding to the OTR. Competition is qualified as any detectable displacement of thiazolidinedione by the candidate for OTR binding. In rats and possibly humans, progesterone, for example, has been observed to possess oxytocin antagonist activity using binding assays (Thornton et al., 1999).

IV. METHODS FOR BLOCKING OXYTOCIN-MEDIATED ACTIONS

The present invention is directed at methods of inhibiting or reducing oxytocin-mediated action and generally treating a subject through the administration of troglitazone, other thiazolidinediones, or thiazolidinedione-like compounds. Consequently, formulations and routes of administration for the compounds are described below.

A. Formulations and Routes for Administration to Patients

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the thiazolidinedione to cells, dissolved or dispersed in a pharmaceutically acceptable carrier or aqueous medium. Such compositions also are referred to as inocula. The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable carrier" or "pharmacologically acceptable carrier" include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The inventors propose that local, regional delivery of thiazolidinedione, such as troglitazone, to a patient who may experience or is experiencing an oxytocin-mediated action, such as uterine contractions in labor or lactation, will be a very efficient method for delivering a therapeutically effective composition to counteract the oxytocin action. Similarly, tocolytic agents may be directed to a particular, affected region of the subject's body. Regional administration includes administration via intra-arterial, intracavity, intravaginal, intravesical, intrathecal, intrapleural, and intraperitoneal routes.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra. The drugs and agents also may be administered parenterally or intraperitoneally. The term "parenteral" is generally used to refer to drugs given intravenously, intramuscularly, or subcutaneously.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intralesional, or even intraperitoneal routes. The preparation of an aqueous composition that contains a thiazolidinedione or thiazolidinedione-like composition as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH, exact concentration of the various components, and the pharmaceutical composition are adjusted according to well known parameters. Suitable excipients for formulation with a thiazolidinedione, such as troglitazone, include croscarmellose sodium, hydroxypropyl methylcellulose, iron oxides (synthetic), magnesium stearate, microcrystalline cellulose, polyethylene glycol 400, polysorbate 80, povidone, silicon dioxide, titanium dioxide, and water (purified).

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

A thiazolidinedione or thiazolidinedione-like composition can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The thiazolidinedione or thiazolidinedione-compound may be formulated within a therapeutic mixture to comprise about 0.0001 to 1.0 milligrams, or about 0.001 to 0.1 milligrams, or about 0.1 to 1.0 or even about 10 milligrams per dose or so. In preferred embodiments, the active oxytocin or oxytocin analog are formulated within a therapeutic mixture to comprise about 0.001 to about 1 milligram. Multiple doses can also be administered.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH, exact concentration of the various components, and the pharmaceutical composition are adjusted according to well known parameters. Suitable excipients for formulation with a thiazolidinedione, such as troglitazone, include croscarmellose sodium, hydroxypropyl methylcellulose, iron oxides (synthetic), magnesium stearate, microcrystalline cellulose, polyethylene glycol 400, polysorbate 80, povidone, silicon dioxide, titanium dioxide, and water (purified).

In addition to the compounds formulated for parenteral administration, such as intravenous or intramuscular injection, other pharmaceutically acceptable forms include, e.g., tablets or other solids for oral administration; liposomal formulations; time release capsules; and any other form currently used, including creams.

One may also use nasal solutions or sprays, aerosols or inhalants in the present invention. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5.

In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Additional formulations that are suitable for other modes of administration include vaginal suppositories and pessaries. A rectal pessary or suppository may also be used.

Suppositories are solid dosage forms of various weights and shapes, usually medicated, for insertion into the rectum, vagina or the urethra. After insertion, suppositories soften, melt or dissolve in the cavity fluids.

In general, for suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

In certain embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%.

The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

B. Therapeutically Effective Amounts of Troglitazone and Other Thiazolidinediones An effective amount of the therapeutic agent is determined based on the intended goal, for example (i) inhibition of uterine contractions or (ii) inhibition of milk letdown. The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

A therapeutically effective amount of a thiazolidinedione, such as troglitazone, that may be combined with a second tocolytic agent as treatment varies depending upon the host treated and the particular mode of administration. In one embodiment of the invention the dose range of thiazolidinedione such as troglitazone used will be about 0.5 mg/kg body weight to about 500 mg/kg body weight. The term "body weight" is applicable when an animal is being treated. When isolated cells are being treated, "body weight" as used herein should read to mean "total cell weight". The term "total weight may be used to apply to both isolated cell and animal treatment. All concentrations and treatment levels are expressed as "body weight" or simply "kg" in this application are also considered to cover the analogous "total cell weight" and "total weight" concentrations. However, those of skill will recognize the utility of a variety of dosage range, for example, 1 mg/kg body weight to 450 mg/kg body weight, 2 mg/kg body weight to 400 mg/kg body weight, 3 mg/kg body weight to 350 mg/kg body weighty, 4 mg/kg body weight to 300 mg/kg body weight, 5 mg/kg body weight to 250 mg/kg body weighty, 6 mg/kg body weight to 200 mg/kg body weight, 7 mg/kg body weight to 150 mg/kg body weighty, 8 mg/kg body weight to 100 mg/kg body weight, or 9 mg/kg body weight to 50 mg/kg body weight. Further, those of skill will recognize that a variety of different dosage levels will be of use, for example, 1 mg/kg, 2 mg/kg, 3 mg/kg, 4 mg/kg, 5 mg/kg, 7.5 mg/kg, 10, mg/kg, 12.5 mg/kg, 15 mg/kg, 17.5 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 120 mg/kg, 140 mg/kg, 150 mg/kg, 160 mg/kg, 180 mg/kg, 200 mg/kg, 225 mg/kg, 250 mg/kg, 275 mg/kg, 300 mg/kg, 325 mg/kg, 350 mg/kg, 375 mg/kg, 400 mg/kg, 450 mg/kg, 500 mg/kg, 550 mg/kg, 600 mg/kg, 700 mg/kg, 750 mg/kg, 800 mg/kg, 900 mg/kg, 1000 mg/kg, 1250 mg/kg, 1500 mg/kg, 1750 mg/kg, 2000 mg/kg, 2500 mg/kg, and/or 3000 mg/kg. Of course, all of these dosages are exemplary, and any dosage in-between these points is also expected to be of use in the invention. Any of the above dosage ranges or dosage levels may be employed for troglitazone or other thiazolidinediones alone or for such a compound in combination with a tocolytic drug.

"Therapeutically effective amounts" or "amount of [a compound] effective" refer to those amounts effective to produce beneficial results, such as inhibition or reduction of oxytocin-mediated actions. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

As is well known in the art, a specific dose level of active compounds such as troglitazone and thiazolidinediones compounds for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

In some embodiments, the troglitazone or thiazolidinediones compound will be administered in combination with a second agent. So long as a dose of second agent that does not exceed previously quoted toxicity levels is not required, the effective amounts of the second agents may simply be defined as those amounts effective to inhibit or reduce oxytocin-mediated actions, when administered to an animal in combination with the thiazolidinedione. This is easily determined by monitoring the animal or patient and measuring those physical and biochemical parameters of health and disease that are indicative of the success of a given treatment. Such methods are routine in animal testing and clinical practice.

C. Combination Therapies.

A major purpose of the invention is to reduce oxytocin-mediated action. Administration of thiazolidinedione or thiazolidinedione-like compounds alone or in combination with other agents is contemplated. Other agents that can be combined with a thiazolidinedione or thiazolidinedione-like compound include other tocolytic agents, such as beta mimetics, magnesium sulfate, prostaglandin inhibitors, and calcium-blocking agents that relax the uterus will reduce or prevent oxytocin-mediated actions that affect uterine contractions, prostaglandin release, and milk letdown.

Various combinations may be employed; thiazolidinedione or a thiazolidinedione-like compound is "A" and the other agent is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like similar result without departing from the spirit and scope of the invention.

Example 1

Materials and Methods

Chemicals: Chemicals were obtained from the following sources: OT and OT antagonist (OTA)=[d(CH$_2$)$_5$, Tyr(Me)$^2$, Thr$^4$, Tyr-NH$_2$$^9$] OVT, Peninsula Laboratories (Belmont, Calif.); ascorbic acid, dexamethasone, and β-glycerophosphate, Sigma.

Cell Culture Conditions: The proper protocols were followed in obtaining human term myometrium tissue from mother's delivering via C-section. Human term pregnant myometrial cells were isolated by collagenase dispersion and were grown in media consisting of Delbecco's modified eagles media (DMEM) supplemented with 10% fetal bovine serum (FBS), and 2% penicillin/streptomycin in a humidified tissue culture incubator at 37° C. under an atmosphere of 5% $CO_2$ and 95% air.

Determination of OTR ligand binding: OTA was monoiodinated as previously described (Hinko and Soloff, 1992). The specific activity of the iodinated peptide was 2000 Ci/mmol at the time of preparation. Whole cell assays for specific OTR binding activity were performed as described previously, using increasing concentrations of [$^{125}$I]OTA (Copland et al., 1999). The concentration of cellular DNA was determined in parallel, using the Hoechst dye H 33258 and a Hoefer DyNA Quant fluorometer according to the manufacturer's instructions.

For competition studies, the appropriate concentration of compound e.g. troglitazone, BRL49653, pioglitazone, estradiol, and vitamin E succinate were incubated in the presence of radiolabeled $^{125}$I-OTA. The specific binding was determined by subtracting total cpm's from nonspecific binding. Specific binding was expressed as a percent of total binding. All points were done in triplicate.

Intracellular calcium levels: Real-time recording of [Ca$^{2+}$]i was performed in single cells using methods and design previously described (Copland et al., 1999). The sensitivity of the assay was 2.5 pg/ml with an intraassay coefficient of variation of 6.3% and the interassay coefficient of variation of 6.9%.

Prostaglandin E2 (PGE2) levels: PGE2 levels in media were measured using a PGE2 enzyme immunoassay (EIA) system from Amersham Life Sciences (Arlington Heights, Ill.) as previously described (Copland, et al., 1999). The sensitivity of the assay was 2.5 pg/ml with an intraassay coefficient of variation of 6.3% and the interassay coefficient of variation of 6.9%.

Statistics: One way analysis of variance followed by Newman-Keuls test were used to determine statistical differences between the means of the different treatment groups (Statview 512 software, BrainPowers, Inc., Calabasas, Calif.). Differences were considered to be significant at P<0.05 level.

Example 2

Interaction Between Troglitazone and an Oxytocin Receptor

In FIG. 1, troglitazone is shown to bind directly to OTR. When added to the binding assay, troglitazone competes directly with $^{125}$I-OTA to decrease levels of detectable binding as the dose of troglitazone is increased. The 50% inhibitory concentration (IC$_{50}$) for troglitazone is 15.7 nM as compared to oxytocin which has an IC$_{50}$=0.58 mM. The IC$_{50}$ for BRL49653 and pioglitazone are approximately 10.6 μM. The IC$_{50}$ for 5β-dihydroprogesterone is approximately 100 μM. Vitamin E succinate and 17β-estradiol demonstrate no affinity for OTR binding.

Example 3

Interference of Oxytocin-Mediated Activities by Troglitazone

Figure 2:
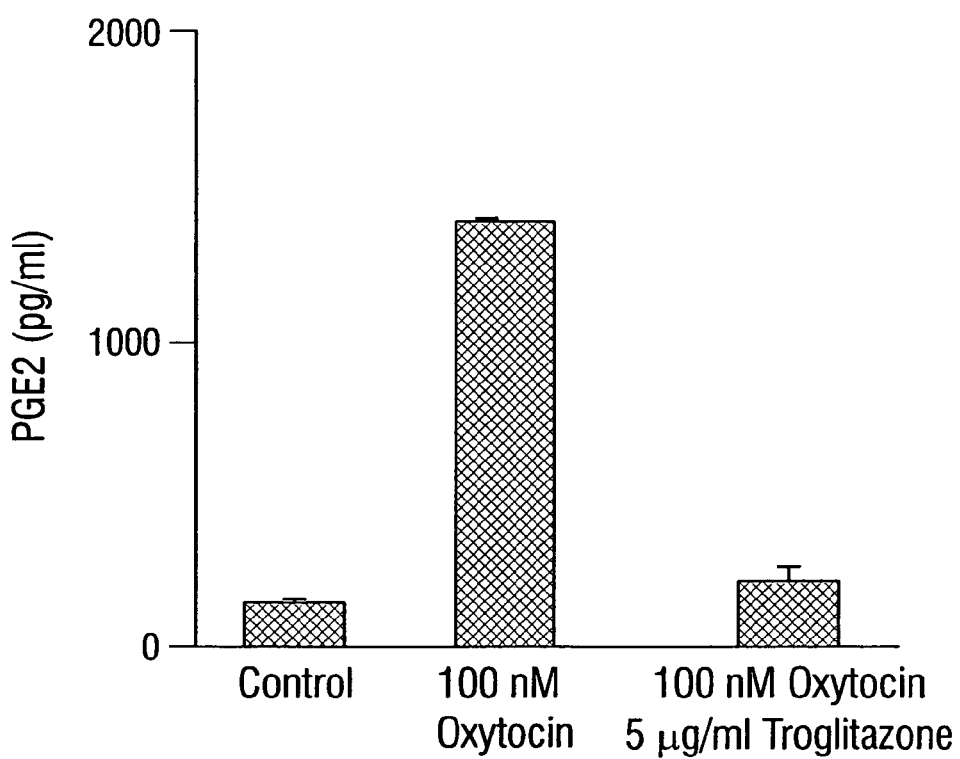
FIG. 2. Prostaglandin $E_2$ levels in primary human myometrial cells. Cells were treated with oxytocin with or without troglitazone for 20 hours. Media was removed and frozen until assayed for PGE2 levels.

Examining prostaglandin E$_2$ (PGE$_2$) synthesis as a functional parameter in primary human myometrial cells has shown a complete block of PGE$_2$ release by oxytocin when 5 μg/ml of troglitazone was added to the culture media minutes prior to oxytocin treatment (FIG. 2).

Figure 3A:
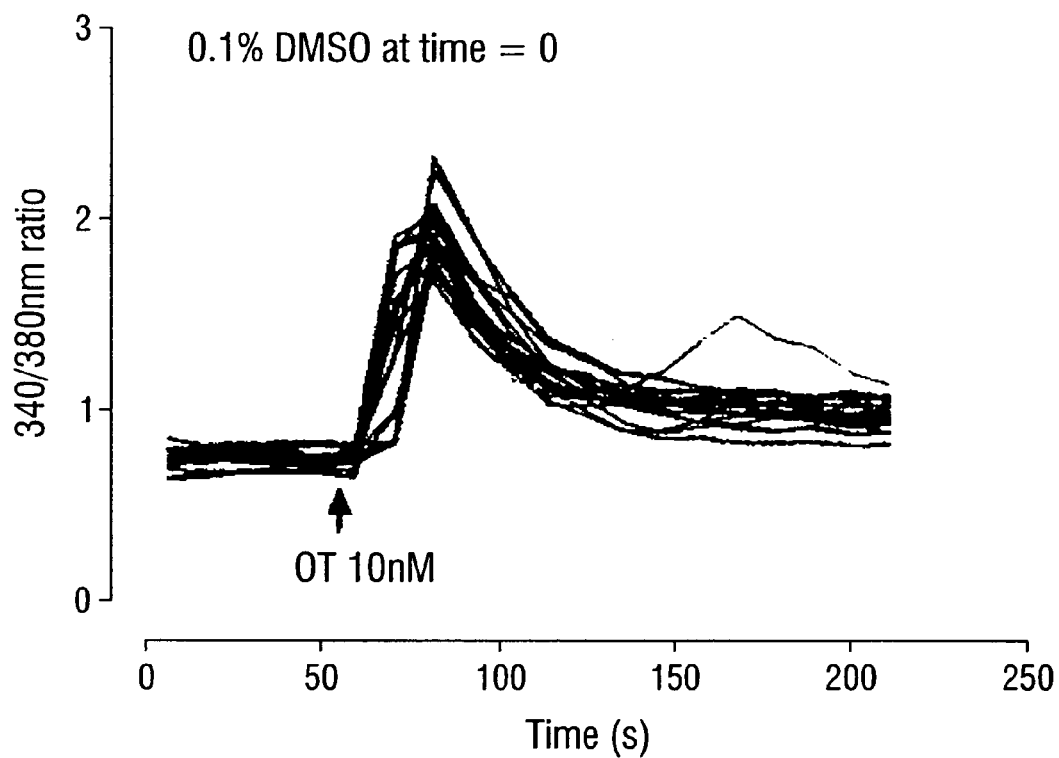
FIGS. 3A-H. Change in intracellular cytoplasmic calcium levels in human term myometrial cells in culture. Each line represents the change in calcium for a single cell. Cells were either pretreated with troglitazone for one minute and then treated with oxytocin, bombesin (BBS), or bradykinin. These three agents cause an increase in intracellular calcium and cause uterine contraction under the correct circumstance. Cells were grown in 10% FBS, DMEM, penicillin/streptomycin resulting in elevated OTR levels. Cells were then put into KRH buffer containing Fura-2. The cells take up Fura-2 allowing for detection in changes of cytoplasmic levels of calcium. Cells were then treated as described for each figure.
Figure 3B:
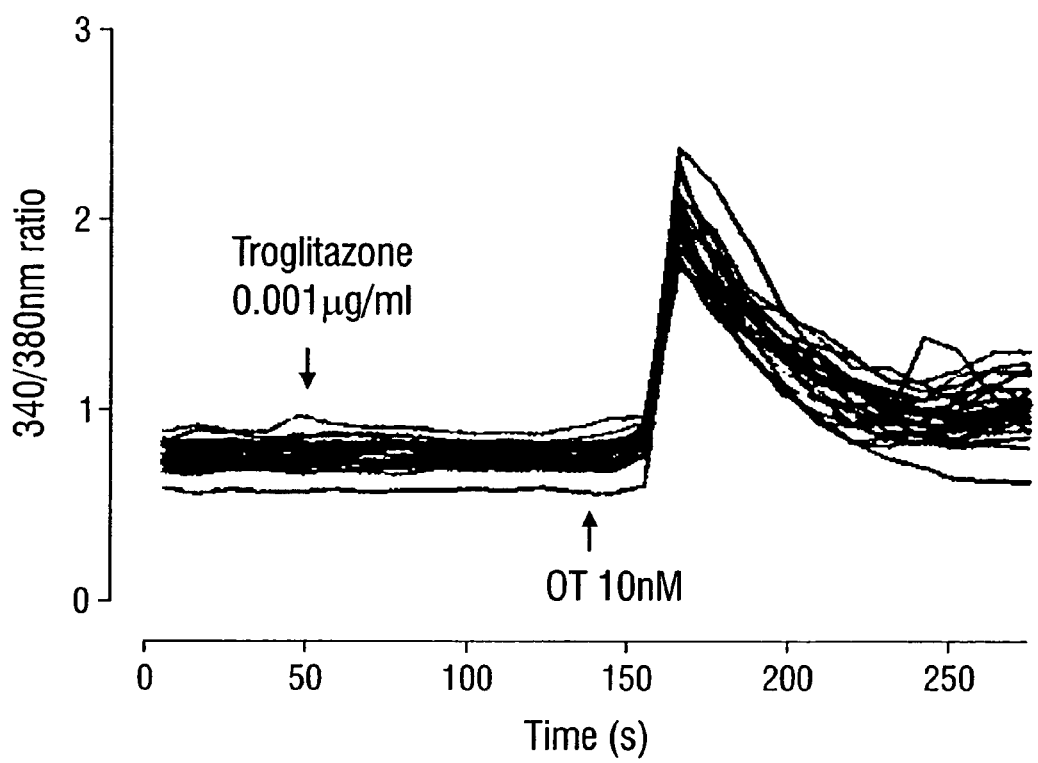
Figure 3C:
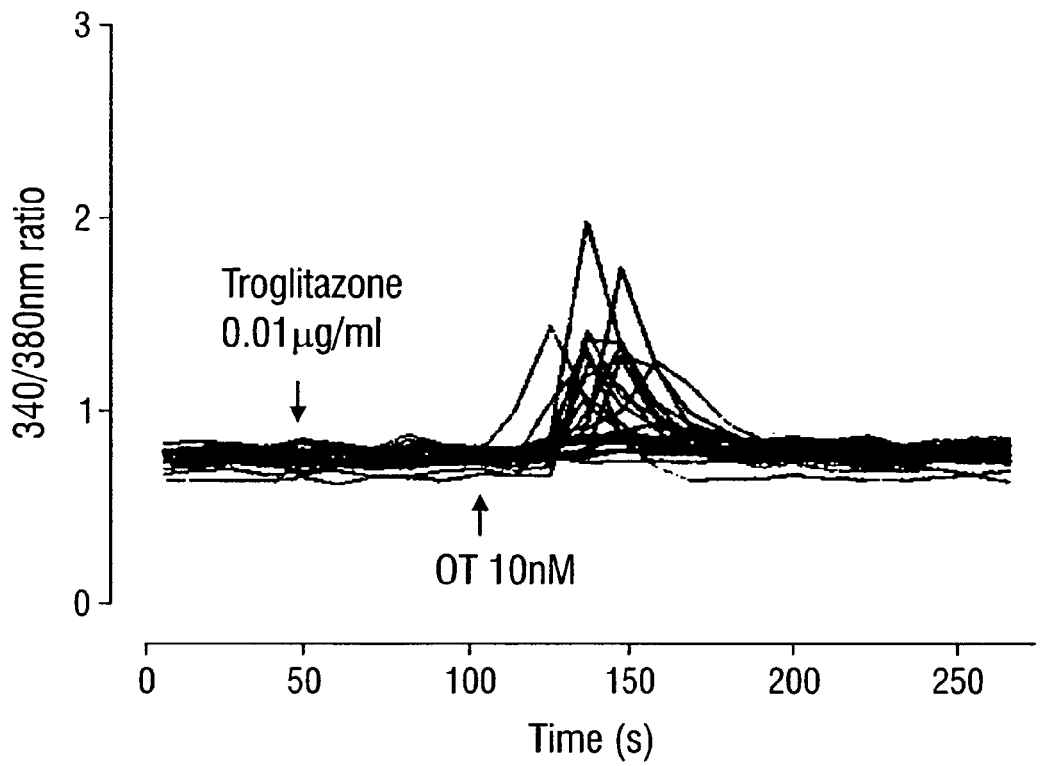
Figure 3D:
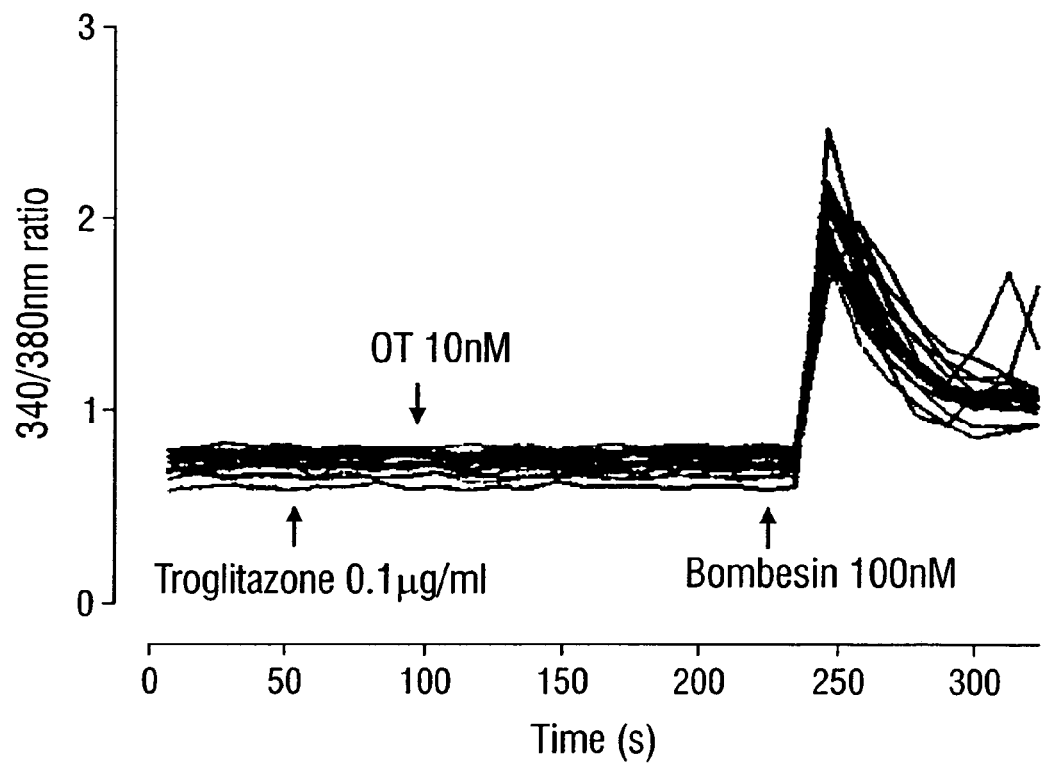
Figure 3E:
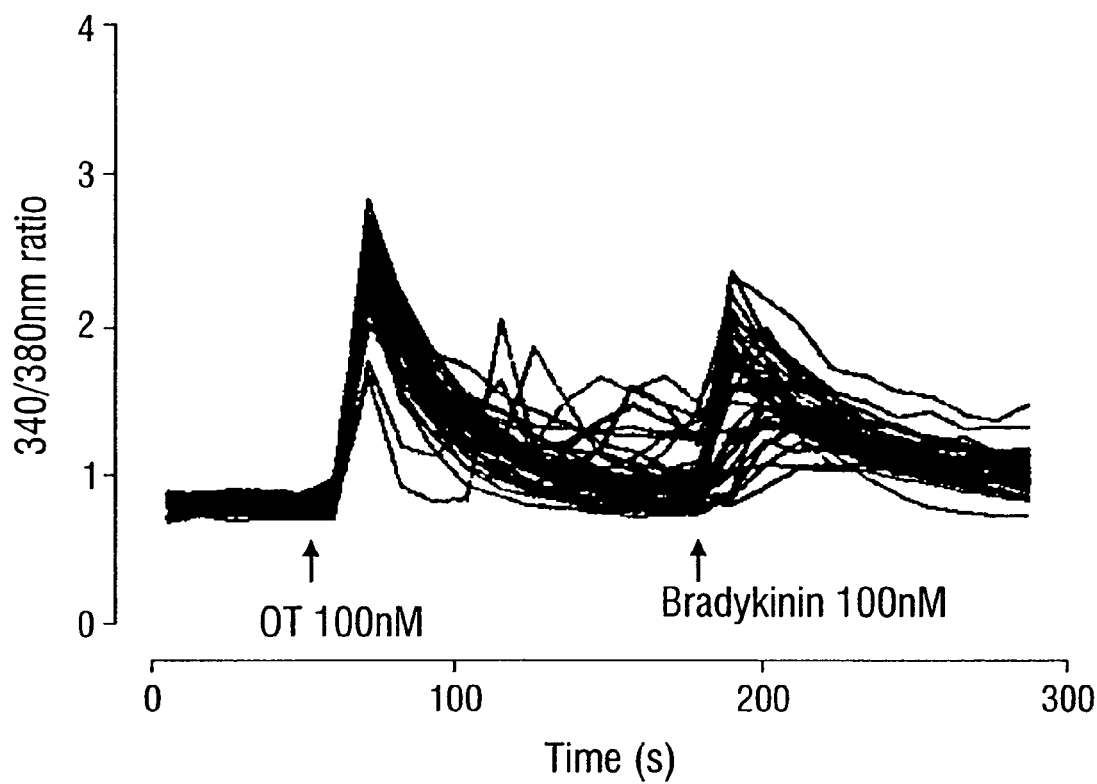
Figure 3F:
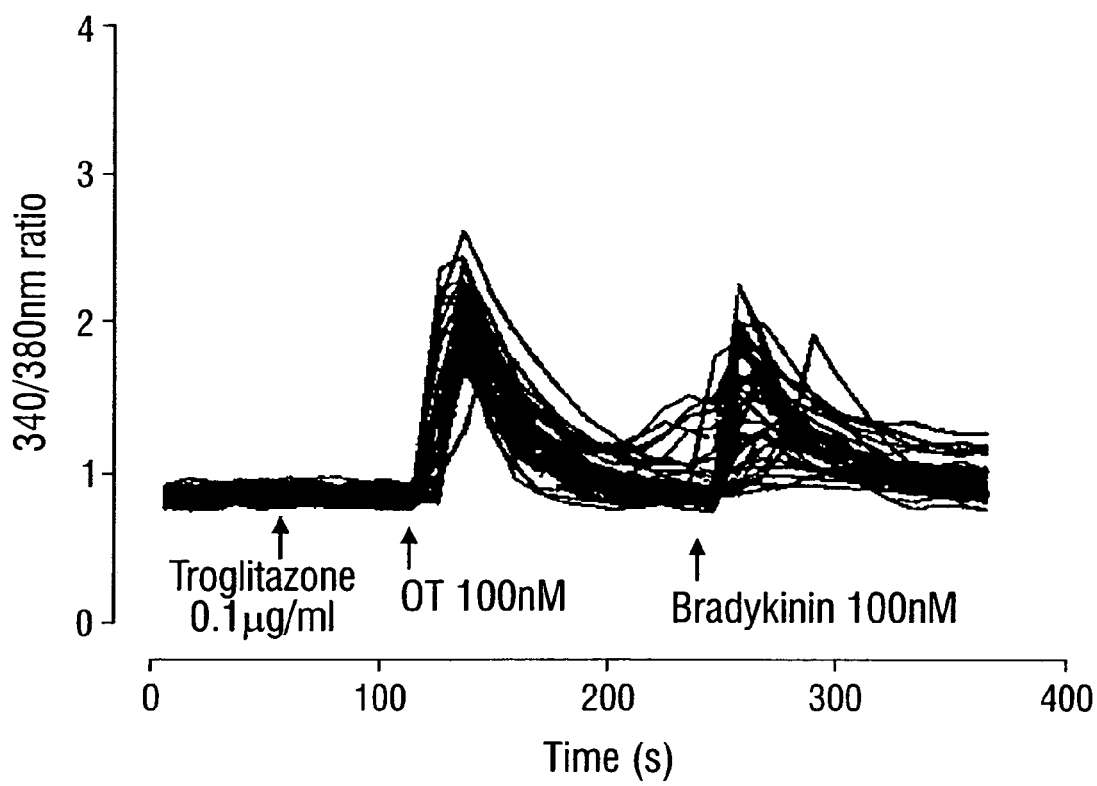
Figure 3G:
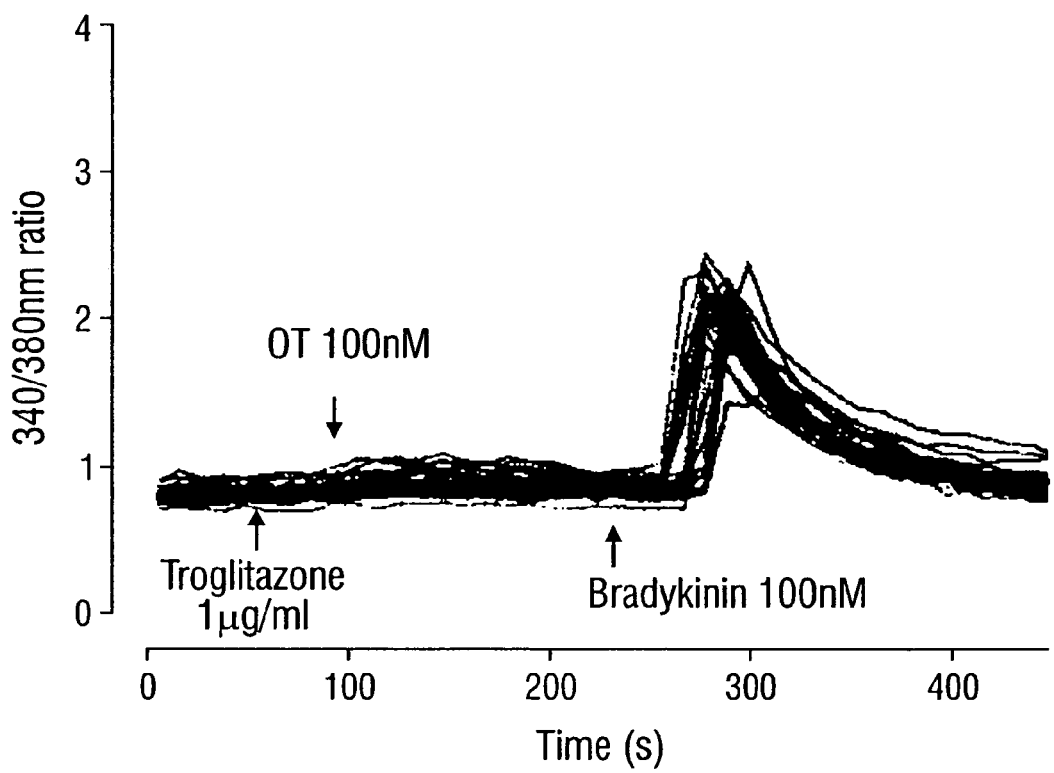
Figure 3H:
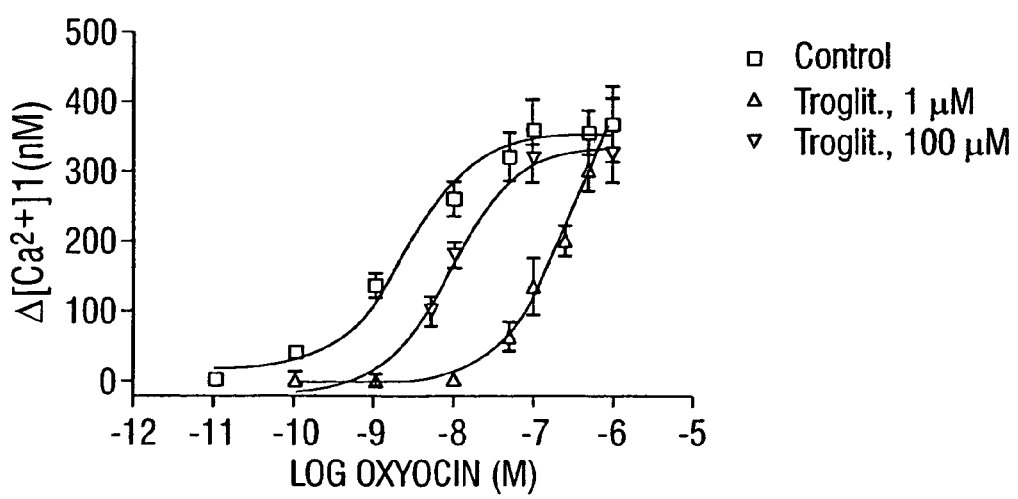

Examination of another functional parameter for oxytocin action, release of intracellular calcium from the endoplasmic reticulum into the cytoplasm of the cell, demonstrates that a 10 nM dose of oxytocin rapidly increases intracellular calcium release (FIG. 3A, each line represents calcium changes from a single cell). Without this increase in intracellular calcium within the myometrial cells, muscle contraction does not occur. In FIG. 3B, a 0.001 μg/ml of troglitazone (2.2 nM) has no effect upon the 10 nM stimulatory dose of oxytocin while in FIG. 3C; a 0.01 μg/ml dose partially inhibits the oxytocin stimulated increase in intracellular calcium. In FIG. 3D, a 0.1 μg/ml dose of troglitazone completely inhibits the oxytocin stimulated increase in intracellular calcium. The effect of troglitazone is specific. 100 nM bombesin in the presence of 0.1 μg/ml troglitazone causes an increase in intracellular calcium levels (FIG. 3D). Bombesin is also a G$_q$ coupled protein as is the OTR. Further evidence of specificity is demonstrated in FIG. 3E, FIG. 3F, and FIG. 3G in which bradykinin stimulation of intracellular calcium release is not inhibited by 1 μg/ml dose of troglitazone while that of 100 nM oxytocin stimulation is inhibited. A dose dependent increase in intracellular calcium is demonstrated in FIG. 3H in response to different concentrations of oxytocin ($10^{-11}$-$10^{-6}$ M, Control). A dose of 0.1 or 1 μM troglitazone demonstrates a dose dependent inhibition of oxytocin induced increases in intracellular calcium. Both doses of troglitazone shift the dose response curve to the right. At high levels of oxytocin in the presence of troglitazone ($10^{-8}$ M OT/107 troglitazone and $10^{-7}$ M OT/$10^{-6}$ M troglitazone), intracellular calcium levels are equivalent to those of OT-stimulation alone. This indicates that troglitazone is a competitive inhibitor as opposed to a noncompetitive inhibitor of oxytocin.

Figure 4A:
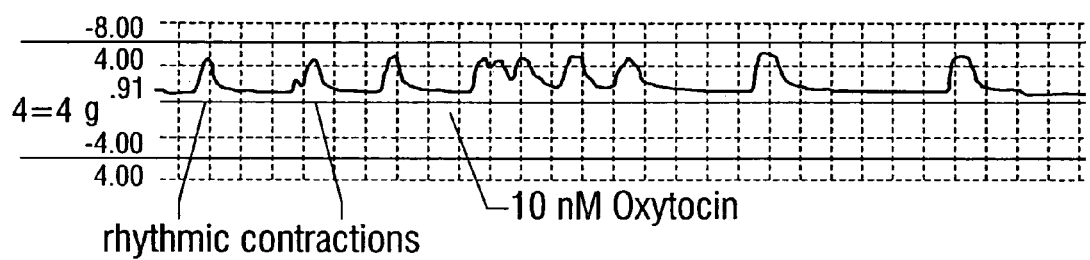
FIG. 4A and FIG. 4B. Measurement of uterine contractions from term human myometrial tissue from C-sections. Rhythmic contractions occur at approximately 3-4 minute intervals as shown in FIGS. 4A and 4B. Upon stimulation with 10 nM oxytocin, myometrium tissue has multiple contractions as shown in FIG. 4A. After approximately 5 minutes (Distance between each vertical axis line represents a minute.), uterine contractions cease in response to 10 nM oxytocin. Pretreatment of myometrium with 10 micrograms/ml (22.6 micromolar) troglitazone for one minute blocks 10 nM oxytocin stimulated contractions (FIG. 4B). After 5 minutes, 100 nM oxytocin was introduced. Contractions occurred in the presence of 100 nM oxytocin demonstrating that the process is reversible. This indicates that competition for binding to the oxytocin receptor occurs.
Figure 4B:
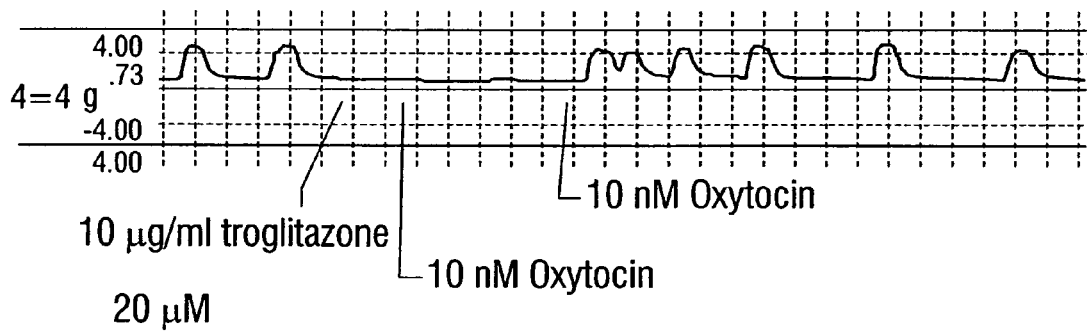

In FIG. 4, term myometrial tissue was obtained from C-section deliveries, and strips of tissue were suspended in a 37° C. PBS bath under a low constant tension. This tension causes rhythmic contractions as demonstrated in FIG. 4A. 10 nM oxytocin causes a rapid increase in contractions that were sustained. After removal of oxytocin, the tissue reverts back to the rhythmic pattern of contraction. In FIG. 4B, a dose of 10 µg/ml of troglitazone inhibited 10 nM oxytocin induced contractions. A 100 nM dose of oxytocin was able to overcome the troglitazone inhibition demonstrating reversibility of troglitazone treatment.

All of the compositions and/or methods disclosed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein (e.g., other thiazolidinediones) while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Copland, Jeng, Strakova, Ives, Hellmich, and Soloff, "Demonstration of functional oxytocin receptors in human breast Hs578T cells and their upregulation through a PKC-dependent pathway." *Endocrinology*, 140:2258, 1999.

Dong, Fang, Kondapaka, Gangula, Wimalawansa, and Yallampalli, "Involvement of calcitonin gene-related peptide in the modulation of human myometrial contractility during pregnancy." *J. Clin. Invest.*, 104:559-565, 1999.

Fuchs, Fuchs, Husslein, Soloff, and Fernstrom, "Oxytocin receptors and human parturition: A dual role for oxytocin in the initiation of labor." *Science*, 215:1396-1398, 1982.

Fuchs, Periyasamy, Alexandrova, and Soloff, "Correlation between oxytocin receptor concentration and responsiveness to oxytocin in pregnant rat myometrium: effects of ovarian steroids." *Endocrinology*, 113:742-749, 1983.

Grazzini, Guillon, Mouillac, and Zingg, "Inhibition of oxytocin receptor function by direct binding of progesterone." *Nature*, 392:509-512, 1998.

Hinko and Soloff, "Characterization of oxytocin receptors in rabbit amnion involved in the production of $PGE_2$". *Endocrinology*, 130:3547-3553, 1992.

Hinko and Soloff, "Up-regulation of oxytocin receptors in rabbit amnion by glucocorticoids. Potentiation by cyclic adenosine 3',5' monophosphate." *Endocrinology*, 133:1511-1519, 1993.

Hoare, Copland, Strakova, Jeng, Ives, Hellmich, and Soloff, "The proximal portion of the cooH terminus of the oxytocin receptor is required for coupling to Gg, but not Gi." *Journal Biological Chemistry*, 274:28682, 1999.

Kimura, Takemura, Nomura, Nobunaga et. al, "Expression of oxytocin receptor in human pregnant myometrium." *Endocrinology*, 137:780-785, 1996.

Larcher, Neculcea, Breton, Arslan, Rozen Russo, and Zingg. "Oxytocin receptor gene expression in the rat uterus during pregnancy and the estrous cycle and in response to gonadal steroid treatment." *Endocrinology*, 136:5350-5356, 1995.

Main, "Preterm Labor." The American College of Obstetricians and Gynecologists Technical Bulletin, No. 206, June, 1995.

McCormick, "The contribution of low birth weight to infant mortality and childhood morbidity." *N. Engl. J. Med.*, 312:82-90, 1985.

Moise, Huhta, Sharif, Ou, Kirshon, Wasserstrum et al., "Indomethacin in the treatment of premature labor: effects on the fetal ductus arteriosus." *N. Engl. J. Med.*, 319:327-331, 1998.

Norton, Merrill, Cooper, Kuller, and Clyman, "Neonatal complications after the administration of indomethacin for preterm labor." *N. Engl. J. Med.*, 329:1602-1607, 1993.

Postina, Kojro, and Fahrenholz, "Separate agonist and peptide antagonist binding sites of the oxytocin receptor defined by their transfer into the $V_2$ vasopressin receptor." *J. Biol. Chem.*, 271:31593-31601, 1996.

Soloff, Alexandrova, Fernstrom, "Oxytocin receptors: Triggers for parturition and lactation?" *Science*, 204:1313-1315, 1979.

Soloff, "Endocrine control of parturition." *Biology of the Uterus* ($2^{nd}$ ed.), Wynn R M, Jollie W P (Eds.), Plenum Press, NY, pp 559-607, 1989.

Strakova and Soloff, "Coupling of oxytocin receptor to G proteins in the rat myometrium during labor: $G_i$-receptor interaction." *Am. J. Physiol.*, 272:E870-E876, 1997.

Strakova, Copland, Lolait, and Soloff, "ERK2 mediates oxytocin-stimulated PGE synthesis." *Am. J. Physiol.*, 274: E634-E641, 1998.

Thornton, Terzidou, Clark, and Blanks, "Progesterone metabolite and spontaneous myometrial contractions in vitro." *The Lancet*, 353:1327-1329, 1999.

Wilkins, Lynch, Mehalek, Berkowitz, and Berkowitz, "Efficacy and side effects of magnesium sulfate and ritodrine as tocolytic agents." *Am. J. Obstet. Gynecol.*, 159:685-689, 1988.

Williams, Bock Evans, Freidinger, et al. "Nonpeptide oxytocin antagonists: analogs of L-371,257 with improved potency." *Bioorganic & Medicinal Chemistry Letters* 9:1311-1316, 1999.

The invention claimed is:

1. A method for reducing an oxytocin-mediated action in a subject comprising administering to the subject an amount of thiazolidinedione effective to reduce the oxytocin-mediated action in the subject, wherein the oxytocin-mediated action is induction of labor in a pregnant subject.

2. The method of claim 1, wherein the subject is a mammal.

3. The method of claim 1, wherein the thiazolidinedione is troglitazone.

4. The method of claim 1, wherein the thiazolidinedione is pioglitazone, or BRL49653.

5. The method of claim 1, wherein the thiazolidinedione is dispersed in a pharmacologically acceptable form.

6. The method of claim 5, wherein said thiazolidinedione is administered locally.

7. The method of claim 5, wherein said thiazolidinedione is administered parenterally.

8. The method of claim 7, wherein said thiazolidinedione is administered intravenously.

9. The method of claim 6, wherein the thiazolidinedione is administered intravaginally.

10. The method of claim 1, further comprising administering a tocolytic agent.

11. The method of claim 10, wherein said tocolytic agent comprises a beta-mimetic, magnesium sulfate, a prostaglandin inhibitor, or a calcium-blocking agent.

12. The method of claim 11, wherein the prostaglandin inhibitor is indomethacin.

13. The method of claim 12, wherein the calcium-blocking agent is nifedipine.

14. The method of claim 10, wherein the tocolytic agent and thiazolidinedione are administered simultaneously.

* * * * *

UNITED STATES PATENT AND TRADEMARK OFFICE
CERTIFICATE OF CORRECTION

PATENT NO. : 7,528,133 B1  Page 1 of 1
APPLICATION NO. : 10/069744
DATED : May 5, 2009
INVENTOR(S) : John A. Copland, III et al.

It is certified that error appears in the above-identified patent and that said Letters Patent is hereby corrected as shown below:

In title page, item (54) Title and in column 1, lines 1-4, delete

"USE OF THIAZOLIDINEDIONES DERIVATIVES FOR PREVENTING UTERINE CONTRACTIONS IN PREMATURE LABOUR OR LACTATION" and insert --CLINICAL USE OF THIAZOLIDINEDIONES ALONE OR IN CONJUNCTION WITH OTHER AGENTS TO BLOCK OXYTOCIN-MEDIATED ACTIONS SUCH AS UTERINE CONTRACTIONS IN PREMATURE LABOR OR LACTATION-- therefor.

In title page, item (57) Abstract, line 10, delete "Caesarian" and insert --Caesarean-- therefor.

Signed and Sealed this

Fourteenth Day of July, 2009

JOHN DOLL
*Acting Director of the United States Patent and Trademark Office*